United States Patent
Paquet et al.

(10) Patent No.: US 6,605,633 B1
(45) Date of Patent: Aug. 12, 2003

(54) IL-8 RECEPTOR ANTAGONISTS

(75) Inventors: Jean-Luc Paquet, Brognon (FR); Martine Barth, Asnieres les Dijon (FR); Didier Pruneau, Pasques (FR); Pierre Dodey, Fontaine les Dijon (FR)

(73) Assignee: Fournier Industrie et Sante, Chenove (FR)

( * ) Notice: Subject to any disclaimer, the term of this patent is extended or adjusted under 35 U.S.C. 154(b) by 0 days.

(21) Appl. No.: 10/130,454

(22) PCT Filed: Nov. 24, 2000

(86) PCT No.: PCT/FR00/03278

§ 371 (c)(1), (2), (4) Date: May 16, 2002

(87) PCT Pub. No.: WO01/38305

PCT Pub. Date: May 31, 2001

(30) Foreign Application Priority Data

Nov. 25, 1999 (FR) ............................................. 99 14837

(51) Int. Cl.$^7$ ...................... A61K 31/40; C07D 209/04; C07D 409/04

(52) U.S. Cl. ...................... 514/414; 514/419; 548/466; 548/469

(58) Field of Search ................................ 548/466, 469; 514/414, 419

(56) References Cited

FOREIGN PATENT DOCUMENTS

| WO | WO 96/18393 | 6/1996 |
|----|-------------|--------|
| WO | WO 99/06354 | 2/1999 |
| WO | WO 00/51984 | 9/2000 |

OTHER PUBLICATIONS

Oppenheim et al. "Properties of the novel proinflammatory supergene intercrine cytokine family". *Annu. Rev.Iimmunology*, vol. 9, pp. 617–648, 1991.

Van Damme. Interleukin–8 and related chemotactic cytokines. *The Cytokines Handbook 2nd ed.* A. W. Thomson, ed., Academic Press, London, pp. 185–208, 1994.

Van Damme et al.. Interleukin–8 and other CXC chemokines.. *The Cytokines Handbook 2nd ed.* A. W. Thomson, ed., Academic Press, London, pp. 271–311, 1994.

Richmond. "Purification of melanoma growth stimulatory activity". *Journal of Cellular Physiology*, vol. 129, pp. 375–384, 1986.

Cheng et al. "The melanoma growth stimulatory activity receptors consists of two proteins", *The Journal of Immunology*, vol. 148, No. 2, pp. 541–546, Jan., 15, 1992.

Ponath. "Chemokine receptor antagonists: novel therapeutics for inflammation and AIDS". *Exp. Opin. Invest. Drugs*, vol. 7, No. 1, pp. 1–18, 1998.

Baggiolini et al. "Interleukin–8, a chemotactic and inflammatory cytokine". *FEBS*, vol. 307, No. 1, pp. 97–101, Jul. 1992.

Miller et al. "Biology and biochemistry of the chemokines: a family of chemotactic and inflammatory cytokines". *Critical Reviews in Immunology*, vol. 12, No. 1,2 , pp. 17–46, 1992.

Seitz et al. "Enhanced production of neutrophile–activating peptie–1/interleukin–8 rheumatoid arthritis." *Journal of Clin. Invest.*, vol. 87, pp. 463–469, Feb. 1991.

Miller et al. "Elevated levels of NAP–1/interleukin–8 are present in the airspaces of patients with the adult respiratory distress syndrome and are associated with increased mortality". *Am. Rev. Resp. Dis.*, vol. 166, pp. 427–432, 1992.

Donnelly et al. "Interleukin–8 and development of adult respiratory distress syndrome in at–risk patient groups". *Lancet*, vol. 341, pp. 643–647, Mar. 13, 1993.

Sekido et al. "Prevention of lung reperfusion injury in rabbits by a monoclonal antibody against interleukin–8". *Letters to Nature*, vol. 365, pp. 654–657, Oct. 14, 1993.

Kukielka et al. "Interleukin–8 gene induction in the myocardium after ischemia and reperfusion in vivo". *Journal of Clinical Investigation*, vol. 95, pp. 89–103, 1995.

Broaddus et al. "Neutralization of IL–8 inhibits neutrophil influx ina rabbit model of endotoxin–inducted pleurisy". *Journal of Immunology*, vol. 152, pp. 2960–2967, 1994.

(List continued on next page.)

*Primary Examiner*—Joseph K. McKane
*Assistant Examiner*—Ebenezer Sackey
(74) *Attorney, Agent, or Firm*—Merchant & Gould P.C.

(57) ABSTRACT

The present invention relates to novel compounds which inhibit the action of CXC chemokines, such as IL-8, Gro, NAP-2, ENA-78 etc., on their receptors, to the process for their preparation and to their use for obtaining drugs.

According to the invention, said compounds are novel indole derivatives selected from the group consisting of:

i) the products of the formula

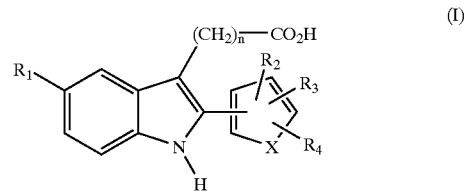

(I)

in which:

X is a double bond —C═C— or a sulfur atom;
$R_1$ is a halogen, a nitro group, a trifluoromethyl group or a $C_1$–$C_3$ alkyl group;
$R_2$, $R_3$ and $R_4$ are each independently a hydrogen atom, a halogen, a $C_1$–$C_3$ alkyl group, a nitro group, a trifluoromethyl group or a cyano group, or $R_2$ and $R_3$ form a fused aromatic ring together with the aromatic ring to which they are attached; and
n is equal to 2 or 3; and ii) esters of the compounds of formula I and addition salts of said compounds with a mineral or organic base.

8 Claims, No Drawings

OTHER PUBLICATIONS

Folkesson et al. "Acid aspiration–induced lung injury in rabbits in mediated by interleukin–8–dependent mechanisms". *Journal of Clin. Invest.*, vol. 96, pp. 107–116, Jul. 1995.

Yokoi et al. "Prevention of endotexemia–induced respiratory distress syndrome–like lung injury in rabbits by a monoclonal antibody to IL–8". *Laboratory Investigation*, vol. 76, No. 3, pp. 375–384, Mar. 1997.

Akahoshi et al. "Essential involvement of interleukin–8 in neutrophil recruitment in rabbits with acute experimental arthritis induced by lippolysaccharide and interleukin–1". *Lymphokine and Cytokine Research*, vol. 13, No. 2, pp. 113–116, 1994.

Nishimura et al. "Attenuation of momosodium urate crystal–induced arthritis in rabbits by a neutralizing antibody against interleukin–8". *Journal of Leukocyte Biology*, vol. 62, pp. 444–449, Oct. 1997.

Wada et al. "Prevention of proteinuria by the administration of anti–interleukin 8 antibody in experimental acute immune complex–induced glomerulonephritis". *Journal of Exp. Med*, vol. 180, pp. 1135–1140, Sep. 1994.

Cacalano et al. "Neutrophil and B cell expansion in mice that lack the murine IL–8 receptor homolog". *Science*, vol. 265, pp. 682–684, Jul. 29, 1994.

Herbert et al. "Interleukin–8: a review". *Cancer Investigation*, vol. 11, No. 6, pp. 743–750, 1993.

Richards et al. "Coexpression of interleukin–8 receptors in head and neck squamous cell carcinoma". *The American Journal of Surgery*, vol. 174, pp. 507–512, Nov. 1997.

IL-8 RECEPTOR ANTAGONISTS

This application is a 371 of PCT/FR00/03278 filed Nov. 24, 2000.

The present invention relates to novel compounds which inhibit the action of CXC chemokines, such as IL-8, Gro, NAP-2, ENA-78 etc., on their receptors, to the process for their preparation and to their use for obtaining drugs.

PRIOR ART

IL-8 (interleukin-8) is a protein of 72 amino acids belonging to the superfamily of proteins capable of attracting leukocytes, said proteins also being referred to as C—X—C cytokines or C—C intercrine cytokines or, more recently, chemokines (Oppenheim et al., *Annu. Rev. Immunol.*, 1991, 9, 617–648). Different names have been attributed to interleukin-8, such as NAP-1 (neutrophil attractant/activation protein 1), NAF (neutrophil activating factor) and T-cell lymphocyte chemotactic factor. Numerous members of the chemokine family have been described as being involved in inflammatory processes and leukocyte migration. The chemokine family is made up of two distinct subfamilies: alpha- and beta-chemokines. Alpha-chemokines, such as IL-8, NAP-2 (neutrophil activating peptide-2), MGSA/Gro or Gro-alpha (melanoma growth stimulatory activity) and ENA-78, all have effects on the attraction and activation of leukocytes and more particularly neutrophils. This subfamily also includes PF-4 (platelet factor-4), beta-thromboglobulin and CTAPIII, which have no effect on neutrophils.

IL-8 was originally identified by its capacity to attract and activate polymorphonuclear leukocytes (neutrophils). More recently, it was shown that the expression of IL-8 was rapidly induced in different tissues or cells, such as macrophages, fibroblasts, endothelial and epithelial cells and even neutrophils, in response to pro-inflammatory cytokines like IL-1 alpha or beta or TNF alpha, or other pro-inflammatory agents like LPS (Van Damme J., *Interleukin-8 and related chemotactic cytokines*; 1994; *The Cytokines Handbook*, 2nd ed., edited by A. W. Thomson, Academic Press, London, pp. 185–208). Furthermore, some literature data have demonstrated high systemic levels of IL-8 in certain inflammatory pathological conditions involving neutrophils, suggesting that IL-8 and other chemokines of the same family may be fundamental mediators of neutrophil activation (Van Damme, *Interleukin-8 and related chemotactic cytokines*; 1994; *The Cytokines Handbook*, 3rd ed., edited by A. W. Thomson, Academic Press, London, pp. 271–311).

Gro-alpha, Gro-beta, Gro-gamma and NAP-2 belong to the chemokine family and, like IL-8, these proteins have also been given different names. Thus Gro-alpha, beta and gamma have been called MGSA (Melanoma Growth Stimulatory Activity) a, b and g respectively (Richmond and Thomas, *J. Cell Physiol.*, 1986, 129, 375–384; Cheng et al., *J. Immunol.*, 1992, 148, 451–456). All these chemokines belong to the group of alpha-chemokines which possess an ELR unit (Aspartate-Leucine-Arginate) upstream of the CXC unit characteristic of this subgroup. These chemokines all bind to the type 2 receptor or CXCR2.

Two IL-8 receptors belonging to the family of receptors with seven transmembrane domains coupled to G proteins have been characterized and cloned: the type A IL-8 receptor (IL-8RA) or CXCR1, which binds IL-8 and GCP-2 with a strong affinity, and the type B IL-8 receptor (IL-8RB) or CXCR2, which has IL-8, GCP-2, Gro-alpha, Gro-beta, Gro-gamma and NAP-2 as specific ligands (Ponath, *Exp. Opin. Invest. Drugs*, 1998, 7, 1–18). These two receptors have an amino acid sequence homology of 77%. Numerous publications have demonstrated abnormally high levels of IL-8 in rheumatoid polyarthritis, septic shock, asthma, mucoviscidosis, myocardial infarction and psoriasis (Baggiolini et al., *FEBS Lett.*, 1992, 307, 97–101; Mille and Krangel, *Crit. Rev. Immunol.*, 1992, 12, 17–46; Oppenheim et al., *Annu. Rev. Immunol.*, 1991, 9, 617–648; Seitz et al, *J. Clin. Invest.*, 1991, 87, 463–469; Miller et al., *Am. Rev. Resp. Dis.*, 1992, 146, 427–432; Donnelly et al., *Lancet*, 1993, 341, 643–647). IL-8 seems to be involved in pulmonary ischemia/reperfusion phenomena (Sekido et al., *Nature*, 1993, 365, 654–657). An antibody directed against IL-8, with the capacity to block the in vitro migration of rabbit neutrophils induced by IL-8, prevents the tissue damages resulting from a pulmonary ischemia/reperfusion process in the rabbit. IL-8 seems to play a major role in the changes due to myocardial hypoxia/reperfusion (Kukielka et al., *J. Clin. Invest.*, 1995, 95, 89–103).

More recently, another study has demonstrated the beneficial effects of an IL-8-neutralizing antibody in a model of pleurisy induced by endotoxins in the rabbit (Broadus et al., *J. Immunol.*, 1994, 152, 2960–2967). The involvement of IL-8 in pulmonary inflammations, and its deleterious role, have been demonstrated using IL-8-neutralizing antibodies in a model of pulmonary attack induced by instilling acid into rabbit's lungs (Folkesson et al., *J. Clin. Invest.*, 1995, 96, 107–116) and in a model of acute respiratory distress syndrome induced by endotoxins (Yokoi et al., *Lab. Invest.*, 1997, 76, 375–384). Other reports have shown similar beneficial effects with IL-8-neutralizing antibodies in animal models of dermatosis, arthritis and glomerulonephritis (Akahoshi et al., *Lymphokine and Cytokine Res.*, 1994, 13, 113–116; Nishimura et al., *J. Leukoc. Biol.*, 1997, 62, 444–449; Wada et al., *J. Exp. Med.*, 1994, 180, 1135–1140). Furthermore, mice deficient in interleukin-8 receptors have been produced by removing the gene coding for the murine IL-8 receptor homologous to the human type 2 receptor (CXCR2) (Cacalano et al., *Science*, 1994, 265, 682–684). Although these mice are healthy, the characteristics of their neutrophils are modified. In fact, their capacity to migrate into the peritoneum is reduced in response to an intraperitoneal injection of thioglycolate.

All these results suggest that chemokines of the IL-8 family are important mediators of the migration and activation of neutrophils and other types of cells, such as endothelial cells, in certain inflammatory conditions. Furthermore, chemokines of the IL-8 family have been described as playing an important role in tumoral growth, metastasis formation and tumoral angiogenesis in numerous types of cancer (Hebert and Baker, *Cancer Invest.*, 1993, 11, 743–750; Richards et al., *Am. J. Surg.*, 1997, 174, 507–512).

Study of the properties of chemokines of the IL-8 family suggests that compounds capable of antagonizing these chemokines at their receptors might have the potential to attenuate the consequences of their action in certain pathological conditions. Thus WO 96-18393 has disclosed compounds derived from 1-benzylindole-2-carboxylic acid which are capable of binding to IL-8 receptors with an inhibitory effect. More recently, according to WO 99-06354, compounds derived from urea or thiourea have also been put forward as IL-8 receptor antagonists.

OBJECT OF THE INVENTION

The invention proposes novel non-peptide compounds which have the property of binding to the CXCR2 receptor of IL-8 and other chemokines of the same family, behaving as antagonists of these receptors.

This property of the compounds according to the invention makes it possible to envisage their use as active principles of drugs for the preventive or curative treatment of diseases involving the receptors of IL-8 and chemokines of the same family, for example rheumatoid polyarthritis, psoriasis or atypical dermatitis, diseases associated with pathological angiogenesis (such as cancer), tumoral cell proliferation and metastasis formation (for example in the case of melanoma), asthma, chronic obstruction of the lungs, acute respiratory distress syndrome, inflammation of the colon, Crohn's disease, ulcerative colitis, gastric ulcer, septic shock, endotoxin shock, Gram-negative septicemia, toxic shock syndrome, cerebral ischemia, cardiac or renal ischemia/reperfusion phenomena, glomerulonephritis, thrombosis, Alzheimer's disease, graft versus host reactions or allograft rejections.

DESCRIPTION

According to the invention, novel compounds are proposed which have the formula

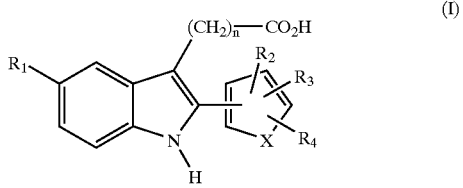

in which:

X is a double bond —C=C— or a sulfur atom;

$R_1$ is a halogen, a nitro group, a trifluoromethyl group or a $C_1$–$C_3$ alkyl group;

$R_2$, $R_3$ and $R_4$ are each independently a hydrogen atom, a halogen, a $C_1$–$C_3$ alkyl group, a nitro group, a trifluoromethyl group or a cyano group, or $R_2$ and $R_3$ form a fused aromatic ring together with the aromatic ring to which they are attached; and n is equal to 2 or 3.

Other novel products to which the invention relates are esters of the compounds of formula I and addition salts of said compounds with a mineral or organic base.

The invention further relates to the use of a compound of formula I or salts thereof for the preparation of a drug for the preventive or curative treatment of diseases dependent on activation of the IL-8 receptors, for example rheumatoid polyarthritis, acute respiratory distress syndrome, psoriasis, Crohn's disease and, more generally, any pathological condition associated with a massive infiltration of neutrophils.

DETAILED DESCRIPTION

As indicated previously, the compounds according to the invention have formula I above. According to the definitions of the substituents $R_1$ to $R_4$, halogen is understood as meaning fluorine, chlorine and bromine atoms, preferably fluorine and chlorine atoms. $C_1$–$C_3$ alkyl group must be understood as meaning methyl, ethyl, propyl, 1-methylethyl and cyclopropyl groups.

The preferred compounds of the invention are those of formula (Ia) below:

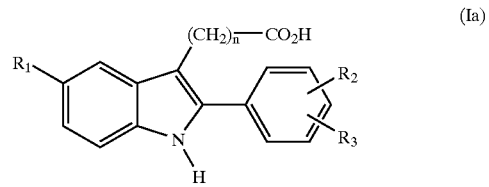

in which:

$R_1$ is a halogen, a nitro group, a trifluoromethyl group or a $C_1$–$C_3$ alkyl group;

$R_2$ and $R_3$ are each independently a hydrogen atom, a halogen or a $C_1$–$C_3$ alkyl group, or they form a fused aromatic ring together with the phenyl ring to which they are attached; and n is equal to 2 or 3, as well as their esters and their addition salts with a mineral or organic base.

The more particularly preferred compounds according to the invention are those of formula I in which X is a double bond —C=C—, $R_1$ is a chlorine atom, $R_2$ and/or $R_3$ are each a chlorine or fluorine atom or a methyl group, preferably in the meta and/or para position of the phenyl ring, and $R_4$ is the hydrogen atom.

Fused aromatic ring is understood as meaning a ring which, together with the aromatic ring carrying the substituents $R_2$, $R_3$ and $R_4$, forms a group containing 2 fused aromatic rings, for example a 2-naphthyl or 1-naphthyl group, the 2-naphthyl group being preferred.

The compounds of formula I, which are acids, can be esterified by organic alcohols, especially $C_2$–$C_3$ aliphatic alcohols such as ethanol or isopropanol (or 1-methylethanol), the preferred esters being the ethyl esters.

The compounds of formula I can be salified with a mineral or organic base. Mineral bases are understood as meaning hydroxides of alkali metals such as sodium hydroxide, potassium hydroxide, lithium hydroxide or alkaline-earth metals such as lime. Organic bases are understood as meaning primary, secondary or tertiary amines, amino alcohols, certain non-toxic nitrogen heterocycles and basic amino acids. The preferred salts are those of sodium or potassium and those of lysine, arginine or 2-amino-2-methylpropane-1,3-diol.

The compounds of formula I can be prepared in particular by a process which comprises the steps consisting in:

a) carrying out a reaction of the Friedel-Crafts type between a cyclic diacid anhydride of the formula

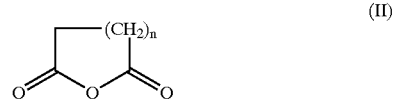

in which n is equal to 2 or 3, and an aromatic derivative of the formula

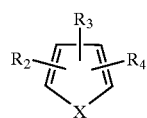
(III)

in which X is a bond —C═C— or a sulfur atom and $R_2$, $R_3$ and $R_4$ are each independently a hydrogen atom, a halogen or a $C_1$–$C_3$ alkyl group, or $R_2$ and $R_3$ form a fused aromatic ring together with the aromatic ring to which they are attached, in an anhydrous solvent, for example dichloromethane, in the presence of a Lewis acid, for example aluminum chloride, at a temperature of between −10 and +50° C., to give a compound of the formula

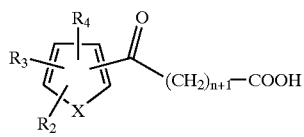
(IV)

in which X, $R_2$, $R_3$, $R_4$ and n are as defined above;

b) esterifying the compound of formula IV above, for example with an aliphatic alcohol of the formula ROH (R=Me or Et), under conventional conditions known to those skilled in the art, to give an ester of the formula

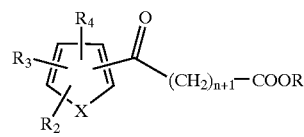
(V)

in which X, R, $R_2$, $R_3$, $R_4$ and n are as defined above;

c) carrying out a Fischer reaction between the compound of formula V and a phenylhydrazine of the formula

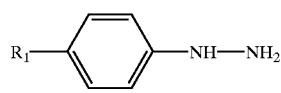
(VI)

in which $R_1$ is a halogen, a trifluoromethyl group or a $C_1$–$C_3$ alkyl group, in the presence of zinc chloride, in a solvent, for example acetic acid, at a temperature of the order of 20 to 80° C., to give the indole derivative of the formula

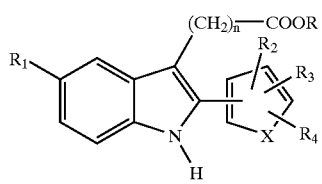
(Ie)

in which X, R, $R_1$, $R_2$, $R_3$, $R_4$ and n are as defined above;

d) hydrolyzing the ester group of the compound of formula Ie obtained above by means of a reaction known to those skilled in the art, for example by reaction with an aqueous-alcoholic solution of sodium hydroxide, to give the corresponding acid derivative of the formula

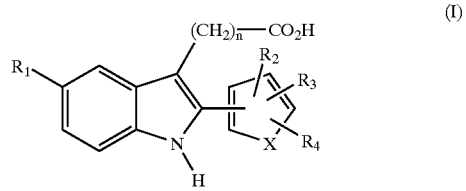
(I)

in which X, $R_1$, $R_2$, $R_3$, $R_4$ and n are as defined above; and e) if necessary, preparing a salt of the acid of formula I by reacting the compound of formula I with a basic mineral or organic compound.

The compounds of formula (I) in which $R_1$ is a nitro group can be obtained by nitrating the corresponding compounds in which $R_1$ is hydrogen by conventional processes well known to those skilled in the art.

The compounds of formula (Ia) can be prepared by the above process using an aromatic derivative of formula (III) in which X is a double bond —C═C—, $R_4$ is a hydrogen atom and $R_2$ and $R_3$ are each independently a hydrogen atom, a halogen or a $C_1$–$C_3$ alkyl group or form a fused aromatic ring together with the phenyl ring to which they are attached.

The above-mentioned compounds of formula (V) can also be obtained directly by carrying out a reaction of the Friedel-Crafts type between an acid chloride of the formula

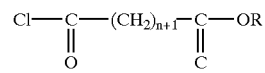

and an aromatic derivative of formula (III) as defined above.

One variant of the process for the preparation of the compounds of formula I comprises carrying out the reactions consisting in:

a) introducing a bromine atom into the 2-position of an indole derivative of formula VII:

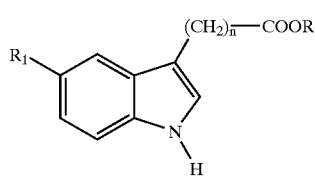
VII in which R is a methyl group, $R_1$ is a halogen, a trifluoromethyl group, a nitro group or a $C_1$–$C_3$ alkyl group and n is 2 or 3, especially by reaction with N-bromosuccinimide, in a solvent such as carbon tetrachloride, to give the compound of the formula

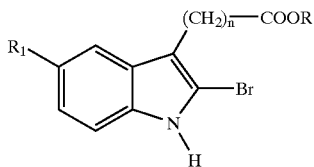

in which n, R and $R_1$ remain unchanged;

b) introducing a substituted or unsubstituted aromatic group to replace the bromine atom in the 2-position of the compound of formula VIII, especially by reaction with a boronic acid of the formula

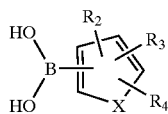

in which $R_2$, $R_3$ and $R_4$ are each independently a hydrogen atom, a $C_1$–$C_3$ alkyl group, a chlorine atom, a fluorine atom, a trifluoromethyl group or a cyano group and X is a double bond —C=C— or a sulfur atom, in a solvent, in the presence of a catalyst such as tetrakis(triphenylphosphine)palladium, to give a compound of the formula

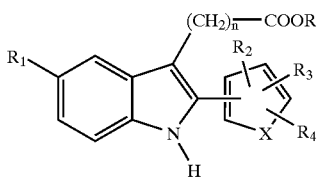

in which X, R, $R_1$, $R_2$, $R_3$, $R_4$ and n are as defined above; and c) hydrolyzing the ester group of the compound of formula Ie, by a procedure analogous to that recommended in stage d) of the process described above, to give the compound of formula I:

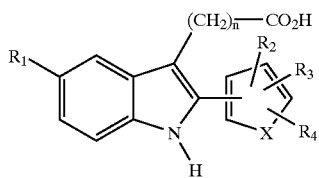

in which X, $R_1$, $R_2$, $R_3$, $R_4$ and n are as defined above.

In one variant of this process, step b) consists in reacting the compound of formula VIII with a tin derivative containing a nitrated aromatic ring, for example trimethyl(4-nitrophenyl)tin, by conventional processes well known to those skilled in the art, to form the compounds of formula (I) in which $R_2$, $R_3$ or $R_4$ is a nitro group.

PREPARATION I

Methyl 4-Fluoro-ε-oxobenzenehexanoate

A suspension of 2.59 g ($19.4.10^{-3}$ mol) of aluminum chloride in 4 ml of dichloromethane is prepared. It is cooled to −5° C. and a mixture of 0.97 ml ($10.3.10^{-3}$ mol) of fluorobenzene and 1.31 ml ($8.4.10^{-3}$ mol) of methyl 6-chloro-6-oxohexanoate in 3 ml of dichloromethane is added gradually, the temperature being maintained between −4 and −7° C. The temperature is then allowed to rise to 20° C. and, after 15 hours, the mixture is hydrolyzed in acidified iced water. It is extracted with dichloromethane and the organic phase obtained is washed with water, dried over magnesium sulfate and concentrated under reduced pressure. The 2 g of crude product recovered in this way are purified by chromatography on silica gel using a petroleum ether/ethyl acetate mixture (96/4) as the eluent to give 1.26 g of the expected product in the form of a white powder (yield=63%).

M.p.=58–59° C.

PREPARATION II

Methyl 3,4-Dichloro-ε-oxobenzenehexanoate

The expected product is obtained in the form of an ochre solid with a yield of 79% by following a procedure analogous to Preparation I and starting from 1,2-dichlorobenzene.

M.p.=41–44° C.

PREPARATION III

Methyl ε-Oxonaphthalene-2-hexanoate

The expected product is obtained in the form of a beige solid with a yield of 53% by following a procedure analogous to Preparation I and starting from naphthalene.

M.p.=58–60° C.

PREPARATION IV

4-Fluoro-δ-oxobenzenepentanoic Acid

A suspension of 22.32 g (0.167 mol) of aluminum chloride in 35 ml of dichloromethane is prepared. It is cooled to 0° C. and a mixture of 8.3 g (0.0728 mol) of glutaric anhydride (dihydro-2H-pyran-2,6(3H)-dione) and 8.4 ml (0.0895 mol) of fluorobenzene in 20 ml of dichloromethane is added slowly. The mixture is stirred for 15 hours at room temperature and then hydrolyzed in acidified iced water. The precipitated product is filtered off, washed with water and then dried under reduced pressure. The crude product is then recrystallized from 90 ml of ethyl acetate to give 8.8 g of the expected product in the form of beige crystals (yield=57.5%).

M.p.=134–136° C.

PREPARATION V

4-Chloro-δ-oxobenzenepentanoic Acid

The expected product is obtained in the form of a brown solid with a yield of 39% by following a procedure analogous to Preparation IV and starting from chlorobenzene.

M.p.=108–110° C.

PREPARATION VI

4-Methyl-δ-oxobenzenepentanoic Acid

The expected product is obtained in the form of a beige solid with a yield of 34% by following a procedure analogous to Preparation IV and starting from toluene.

M.p.=131–133° C.

PREPARATION VII

Ethyl 4-Fluoro-δ-oxobenzenepentanoate

A suspension of 8.76 g ($41.7.10^{-3}$ mol) of the acid obtained according to Preparation IV in 80 ml of ethanol is prepared and 1.33 ml of pure sulfuric acid are added. The mixture is refluxed for 5 hours, with stirring. The reaction medium is subsequently concentrated under reduced pressure and then taken up in ethyl ether. This organic phase is washed with water, then with dilute sodium hydroxide solution and then again with water. After drying over magnesium sulfate, the solvent is driven off under reduced pressure to give 9.65 g of the expected product in the form of a pale orange solid (yield=97%).

M.p.=46–47° C.

PREPARATION VIII

Ethyl 4-Chloro-δ-oxobenzenepentanoate

The expected product is obtained in the form of a brown solid with a yield of 87% by following a procedure analogous to Preparation VII and starting from the acid obtained according to Preparation V.

M.p.=45–48° C.

PREPARATION IX

Ethyl 4-Methyl-δ-oxobenzenepentanoate

The expected product is obtained in the form of a brown solid with a yield of 65% by following a procedure analogous to Preparation VII and starting from the acid obtained according to Preparation VI.

M.p.=36–38° C.

EXAMPLE 1

5-Bromo-2-phenyl-1H-indole-3-butanoic Acid a) Ethyl ε-[(E)-2-(4-Bromophenyl)hydrazono]benzenehexanoate A mixture of 1.91 g ($8.55.10^{-3}$ mol) of 4-bromophenylhydrazine hydrochloride and 0.73 g ($8.9.10^{-3}$ mol) of sodium acetate in 17 ml of water is prepared and 2.05 ml ($35.8.10^{-3}$ mol) of acetic acid are added. This mixture is subsequently heated to 70° C., with stirring, and a suspension of 2.0 g ($8.54.10^{-3}$ mol) of ethyl ε-oxobenzenehexanoate in 27 ml of water is then added slowly. The reaction mixture is stirred at 70–80° C. for 45 min and then at room temperature for 12 hours, after which it is extracted with 2 times 50 ml of ethyl acetate. The organic phase is washed with water, dried over magnesium sulfate and concentrated under reduced pressure to give 3.38 g of the expected compound, which is used directly in the next step.

b) 5-Bromo-2-phenyl-1H-indole-3-butanoic Acid

A mixture of 0.6 g of zinc chloride and 1.78 g of the compound obtained in stage a) above in 4.4 ml of acetic acid is prepared. This reaction medium is heated at 75–85° C. for 3 hours and then cooled to room temperature (about 20° C.). 20 ml of water are added, followed by 40 ml of ethyl acetate. The aqueous phase is separated off and re-extracted with 30 ml of ethyl acetate and the combined organic phases are washed with water, dried over magnesium sulfate and concentrated under reduced pressure to give 1.74 g of an oily product (ester of the expected acid), which is taken up with 10 ml of a 10% solution of sodium hydroxide in ethanol. This mixture is refluxed for 30 min and then cooled to 20° C. 40 ml of water are added and the ethanol is driven off under reduced pressure at 40–45° C. The residual basic aqueous phase is washed with 10 ml of ethyl acetate and then acidified to pH 1 with dilute hydrochloric acid solution and extracted with twice 75 ml of ethyl acetate. This organic phase is washed with water, dried and concentrated under reduced pressure to give 1.8 g of crude product, which is purified by chromatography on silica gel using a hexane/ethyl acetate mixture (7/3) as the eluent; this purification yields 600 mg of the expected acid in the form of a pink solid (yield=38%).

M.p.=155–157° C.

EXAMPLE 2

5-Chloro-2-phenyl-1H-indole-3-propionic Acid

The expected acid is obtained in the form of a white solid with a yield of 11% by following a procedure analogous to Example 1 and starting from 4-chlorophenylhydrazine and ethyl δ-oxobenzenepentanoate.

M.p.=167° C.

EXAMPLE 3

5-Chloro-2-phenyl-1H-indole-3-butanoic Acid

The expected acid is obtained in the form of a white solid with a yield of 19% by following a procedure analogous to Example 1 and starting from 4-chlorophenylhydrazine.

M.p.=169–170° C.

EXAMPLE 4

5-Fluoro-2-phenyl-1H-indole-3-butanoic Acid

The expected acid is obtained in the form of a beige solid with a yield of 15% by following a procedure analogous to Example 1 and starting from 4-fluorophenylhydrazine.

M.p.=156–157° C.

EXAMPLE 5

5-(Trifluoromethyl)-2-phenyl-1H-indole-3-butanoic Acid

The expected acid is obtained in the form of an orange solid with a yield of 12% by following a procedure analogous to Example 1 and starting from 4-(trifluoromethyl)phenylhydrazine.

M.p.=144° C.

PREPARATION X

Ethyl 5-Chloro-2-(4-fluorophenyl)-1H-indole-3-propionate

A mixture of 13.9 g ($40.3.10^{-3}$ mol) of the ester obtained according to Preparation VII, 10.8 g ($60.4.10^{-3}$ mol) of 4-chlorophenylhydrazine hydrochloride and 5.5 g ($40.3.10^{-3}$ mol) of zinc chloride in 80 ml of acetic acid is prepared. This mixture is heated to 65–70° C. and stirred at this temperature for 18 hours. After cooling, the reaction medium is filtered and the filtrate is hydrolyzed in cold water. The precipitated organic compound is extracted with 2 times 150 ml of ethyl acetate. The organic phase obtained is washed with water, dried over magnesium sulfate and concentrated under reduced pressure to give 15 g of crude product, which is recrystallized from a diethyl ether/petroleum ether mixture. This gives 8.2 g of product, which is purified again by chromatography on silica gel using a toluene/ethyl acetate mixture (95/5) as the eluent to give 6.93 g of the expected product in the form of a yellow solid (yield=50%).

M.p.=104–105° C.

EXAMPLE 6

5-Chloro-2-(4-fluorophenyl)-1H-indole-3-propionic Acid

A mixture of 500 mg ($1.45.10^{-3}$ mol) of the ester obtained according to Preparation X in 10 ml of dioxane is prepared. 3 ml of 3 N sodium hydroxide soluti on are added and the reaction medium is refluxed for 2 hours. The solvent is then removed under reduced pressure and the residue is taken up in 30 ml of water. The solution obtained is acidified with N hydrochloric acid. The precipitate formed is extracted with 2 times 50 ml of ethyl acetate. The combined organic phases are washed with water, dried over magnesium sulfate and then concentrated under reduced pressure. The crude product is recrystallized from an ethyl acetate/petroleum ether mixture to give 200 mg of the expected acid in the form of a beige powder (yield=43.5%).

M.p.=153–154° C.

PREPARATION XI

Ethyl 5-Chloro-2-(4-chlorophenyl)-1H-indole-3-propionate

The expected ester is obtained in the form of a brown oil with a yield of 35% by following a procedure analogous to Preparation X and starting from the compound obtained according to Preparation VIII.

$^1$H NMR (CDCl$_3$, 300 MHz) δ: 8.09 (broad s, 1H); 7.90 (d, J=8.4 Hz, 1H); 7.58 (d, J=2.2 Hz, 1H); 7.47 (m, 2H); 7.43 (d, J=8.4 Hz, 1H); 7.28 (d, J=8.4 Hz, 1H); 7.16 (dd, J=8.4 Hz, J=2.2 Hz, 1H); 4.16 (q, J=7 Hz, 2H); 3.18 (t, J=8 Hz, 2H); 2.65 (t, J=8 Hz, 2H); 1.23 (t, J=7 Hz, 3H).

EXAMPLE 7

5-Chloro-2-(4-chlorophenyl)-1H-indole-3-propionic Acid

The expected acid is obtained in the form of a beige solid with a yield of 40% by following a procedure analogous to Example 6 and starting from the compound obtained according to Preparation XI.

M.p.=187–190° C.

PREPARATION XII

Ethyl 5-Chloro-2-(4-methylphenyl)-1H-indole-3-propionate

The expected ester is obtained in the form of a brown paste with a yield of 97% by following a procedure analogous to Preparation X and starting from the compound obtained according to Preparation IX.

$^1$H NMR (CDCl$_3$, 300 MHz) δ: 8.1 (broad s, 1H); 7.58 (d, J=1.8 Hz, 1H); 7.42 (dt, J=8.1 Hz, J=1.8 Hz, 2H); 7.29 (d, J=8 Hz, 2H); 7.25 (d, J=8.8 Hz, 1H); 7.14 (dd, J=8.8 Hz, J=1.8 Hz, 1H); 4.20 (q, J=7 Hz, 2H); 3.20 (t, J=8 Hz, 2H); 2.70 (t, J=8 Hz, 2H); 1.23 (t, J=7 Hz, 3H).

EXAMPLE 8

5-Chloro-2-(4-methylphenyl)-1H-indole-3-propionic Acid

The expected acid is obtained in the form of a beige solid with a yield of 40% by following a procedure analogous to Example 6 and starting from the compound obtained according to Preparation XII.

M.p.=177–178° C.

PREPARATION XIII

Methyl 5-Chloro-2-(4-chlorophenyl)-1H-indole-3-butanoate

The expected product is obtained in the form of a light brown solid with a yield of 90% by following a procedure analogous to Preparation X and starting from methyl 4-chloro-ε-oxobenzenehexanoate.

M.p.=47–48° C.

EXAMPLE 9

5-Chloro-2-(4-chlorophenyl)-1H-indole-3-butanoic Acid

The expected acid is obtained in the form of a beige solid with a yield of 20% by following a procedure analogous to Example 6 and starting from the product obtained according to Preparation XIII.

M.p.=194–197° C.

PREPARATION XIV

Methyl 5-Chloro-2-(3,4-dichlorophenyl)-1H-indole-3-butanoate

The expected ester is obtained in the form of a pink solid with a yield of 26% by following a procedure analogous to Preparation X and starting from the compound obtained according to Preparation II.

M.p.=285° C. (decomposition).

EXAMPLE 10

5-Chloro-2-(3,4-dichlorophenyl)-1H-indole-3-butanoic Acid

The expected acid is obtained in the form of a brown solid with a yield of 39% by following a procedure analogous to Example 6 and starting from the compound obtained according to Preparation XIV.

M.p.=187–188° C.

PREPARATION XV

Ethyl 5-Methyl-2-phenyl-1H-indole-3-butanoate

The expected ester is obtained in the form of a brown solid with a yield of 58% by following a procedure analogous to Preparation X and starting from ethyl ε-oxobenzenehexanoate and 4-methylphenylhydrazine hydrochloride.

M.p.=96–98° C.

EXAMPLE 11

5-Methyl-2-phenyl-1H-indole-3-butanoic Acid

The expected acid is obtained in the form of a brown solid with a yield of 93% by following a procedure analogous to Example 6 and starting from the compound obtained from Preparation XV.

M.p.=150–152° C.

PREPARATION XVI

Methyl 5-Chloro-2-(4-fluorophenyl)-1H-indole-3-butanoate

The expected product is obtained in the form of a brown oil with a yield of 86% by following a procedure analogous to Preparation X and starting from the compound obtained according to Preparation I.

M.p.=285° C. (decomposition). $^1$H NMR (DMSO, 300 MHz) δ: 11.4 (broad s, 1H); 7.66 (d, J=8 Hz, 1H); 7.64 (d, J=8 Hz, 1H); 7.63 (d, J=2.4 Hz, 1H); 7.38 (d, J=8.8 Hz, 1H); 7.35 (d, J=8 Hz, 1H); 7.33 (d, J=8 Hz, 1H); 7.09 (dd, J=8.8 Hz, J=2.4 Hz, 1H); 3.55 (s, 3H); 2.8 (t, J=7.3 Hz, 2H); 2.37 (t, J=7.3 Hz, 2H); 1.85 (quint, J=7.3 Hz, 2H).

EXAMPLE 12

5-Chloro-2-(4-fluorophenyl)-1H-indole-3-butanoic Acid

The expected product is obtained in the form of a brown solid with a yield of 53% by following a procedure analogous to Example 6 and starting from the compound obtained according to Preparation XVI.

M.p.=190–192° C.

PREPARATION XVII

Methyl 5-Chloro-2-(2-naphthyl)-1H-indole-3-butanoate

The expected product is obtained in the form of an orange paste with a yield of 65% by following a procedure analogous to Preparation X and starting from the compound obtained according to Preparation III.

$^1$H NMR (CDCl$_3$, 300 MHz) δ: 8.2 (broad s, 1H); 8.01 (s, 1H); 7.91 (m, 3H); 7.68 (d, J=8.1 Hz, 1H); 7.62 (s, 1H); 7.53 (m, 2H); 7.31 (dd, J=8.8 Hz, J=2.2 Hz, 1H); 7.16 (dt, J=6.6 Hz, J=2 Hz, 1H); 3.55 (s, 3H); 2.98 (t, J=7.3 Hz, 2H); 2.37 (t, J=7.3 Hz, 2H); 2.05 (quint, J=7.3 Hz, 2H).

EXAMPLE 13

5-Chloro-2-(2-naphthyl)-1H-indole-3-butanoic Acid

The expected product is obtained in the form of a brown solid with a yield of 79% by following a procedure analogous to Example 6 and starting from the compound obtained according to Preparation XVII.

M.p.=180–185° C.

EXAMPLE 14

2-Phenyl-5-nitro-1H-indole-3-butanoic Acid

A solution of 1.19 g (4.10$^{-3}$ mol) of sodium nitrate in 50 ml of concentrated sulfuric acid is added at 0–5° C., with stirring, to a solution of 3.67 g (13.15.10$^{-2}$ mol) of 2-pheny-1H-indole-3-butanoic acid in 200 ml of concentrated sulfuric acid. Stirring is maintained at 5° C. for 20 min and the reaction medium is then poured into a mixture of water and ice. The yellow precipitate formed is filtered off and washed on the filter with water and with a small amount of petroleum ether. The product is then dried under reduced pressure and purified by chromatography on silica gel using a hexane/ethyl acetate mixture (1/1) as the eluent to give 1.3 g of the expected product in the form of a yellow solid with a yield of 30%.

M.p.=145° C.

EXAMPLE 15

Sodium 5-Chloro-2-4-fluorophenyl)-1H-indole-3-butanoate

A suspension of 1 g (3.15.10$^{-3}$ mol) of the acid obtained according to Example 12 in 100 ml of water is prepared and 3.15 ml of N sodium hydroxide solution are added. The mixture is stirred for 30 min and then filtered on a 0.45 μm filter. The filtrate is lyophilized to give 1.05 g of the expected product in the form of a fine white solid (yield=98%).

M.p.=160–162° C.

PREPARATION XVIII

Ethyl 3,4-Dichloro-δ-oxobenzenepentanoate

The expected product is obtained in the form of a brown oil (yield=47%) by following a procedure analogous to Preparation VII and starting from 3,4-dichloro-δ-oxobenzenepentanoic acid.

NMR (300 MHz, CDCl$_3$) δ: 8.05 (d, J=1.5 Hz, 1H); 7.80 (dd, J=1.5 Hz, J=8.1 Hz, 1H); 7.56 (d, J=8.1 Hz, 1H); 4.13 (q, J=7.4 Hz, 2H); 3.02 (t, J=6.6 Hz, 2H); 2.42 (t, J=6.6 Hz, 2H); 2.05 (quint, J=6.6 Hz, 2H); 1.25 (t, J=7.4 Hz, 3H).

PREPARATION XIX

Ethyl 5-Chloro-2-(3,4-dichlorophenyl)-1H-indole-3-propionate

The expected product is obtained in the form of an orange paste (yield=55%) by following a procedure analogous to Preparation X and starting from the compound obtained according to Preparation XVIII.

NMR (300 MHz, CDCl$_3$) δ: 8.1 (s, 1H); 7.64 (d, J=1.5 Hz, 1H); 7.58 (d, J=2.2 Hz, 1H); 7.55 (d, J=8.8 Hz, 1H); 7.39 (dd, J=2.2 Hz, J=8.8 Hz, 1H); 7.28 (d, J=8.8 Hz, 1H); 7.17 (dd, J=1.4 Hz, J=8.8 Hz, 1H); 4.12 (q, J=8.1 Hz, 2H); 3.18 (m, 2H); 2.64 (m, 2H); 1.25 (t, J=8.1 Hz, 3H).

EXAMPLE 16

5-Chloro-2-(3,4-dichlorophenyl)-1H-indole-3-propionic Acid

The expected product is obtained in the form of an off-white solid (yield=36%) by following a procedure analogous to Example 6 and starting from the compound obtained according to Preparation XIX.

M.p.=150–152° C.

PREPARATION XX

Methyl 5-Chloro-2-(4-bromophenyl)-1H-indole-3-butanoate

The expected product is obtained in the form of an orange solid (yield=89%) by following a procedure analogous to Preparation X and starting from methyl 4-bromo-ε-oxobenzenehexanoate.

M.p.=124–126° C.

EXAMPLE 17

5-Chloro-2-(4-bromophenyl)-1H-indole-3-butanoic Acid

The expected product is obtained in the form of a white solid (yield=93%) by following a procedure analogous to Example 6 and starting from the compound obtained according to Preparation XX.

M.p.=194–195° C.

PREPARATION XXI

Methyl 5-Chloro-2-(4-cyanophenyl)-1H-indole-3-butanoate

A mixture of 480 mg (1.18.10$^{-3}$ mol) of the ester obtained according to Preparation XX, 870 mg (9.7.10$^{-3}$ mol) of cuprous cyanide and 2 ml of N-methyl-2-pyrrolidone is prepared and refluxed for 3 hours. The reaction medium is then cooled and 10 ml of water are added. The mixture is stirred at room temperature for 15 minutes and 8 ml of ethylenediamine are then added. The mixture is subsequently extracted three times with toluene and the combined organic phases are dried and concentrated under reduced pressure. The evaporation residue is purified by chromatography on silica gel using a hexane/ethyl acetate mixture (80/20; v/v) as the eluent to give 220 mg of the expected product in the form of a fine white solid (yield=53%).

M.p.=182–185° C.

EXAMPLE 18

5-Chloro-2-(4-cyanophenyl)-1H-indole-3-butanoic Acid

The expected product is obtained in the form of a pale yellow solid (yield=22%) by following a procedure analogous to Example 6 and starting from the compound obtained according to Preparation XXI.

M.p.=214–215° C.

PREPARATION XXII

Methyl 3,4-Difluoro-ε-oxobenzenehexanoate

The expected product is obtained in the form of a yellow solid (yield=46%) by following a procedure analogous to Preparation I and starting from 1,2-difluorobenzene.

M.p.=41–43° C.

PREPARATION XXIII

Methyl 5-Chloro-2-(3,4-difluorophenyl)-1H-indole-3-butanoate

The expected product is obtained in the form of a white solid (yield=70%) by following a procedure analogous to Preparation X and starting from the compound obtained according to Preparation XXII.

M.p.=127–128° C.

EXAMPLE 19

5-Chloro-2-(3,4-difluorophenyl)-1H-indole-3-butanoic Acid

The expected product is obtained in the form of a white solid (yield=86%) by following a procedure analogous to Example 6 and starting from the ester obtained according to Preparation XXIII.

M.p.=185–186° C.

PREPARATION XXIV

Methyl 2-Bromo-5-chloro-1H-indole-3-butanoate

A solution of 2.25 g ($8.94.10^{-3}$ mol) of methyl 5-chloro-1H-indole-3-butanoate in 85 ml of carbon tetrachloride is prepared and 1.75 g ($9.83.10^{-3}$ mol) of N-bromosuccinimide are added. The reaction mixture is refluxed for 1 hour, with stirring, and then cooled to room temperature and filtered. The solid is washed with carbon tetrachloride and the filtrates are concentrated under reduced pressure. The evaporation residue is purified by chromatography on silica gel using a petroleum ether/ethyl acetate mixture (9/1; v/v) as the eluent to give 2.11 g of the expected product in the form of a beige solid (yield=71%).

M.p.=98° C.

PREPARATION XXV

Methyl 5-Chloro-2-(4-chloro-3-fluorophenyl)-1H-indole-3-butanoate

A solution of 0.4 g ($1.21.10^{-3}$ mol) of the compound obtained according to Preparation XXIV and 0.32 g ($1.83.10^{-3}$ mol) of 4-chloro-3-fluorophenylboronic acid in 14 ml of ethanol and 14 ml of toluene is prepared. 0.16 g ($3.75.10^{-3}$ mol) of lithium chloride, 70 mg ($6.10^{-5}$ mol) of tetrakis(triphenylphosphine)palladium and 3 ml ($3.10^{-3}$ mol) of 1M sodium carbonate solution are then added, with stirring. The reaction mixture is subsequently refluxed for 14 hours, with stirring, and the solvents are then driven off under reduced pressure. The residual solid is purified by chromatography on silica gel using a petroleum ether/ethyl acetate mixture (9/1; v/v) as the eluent to give 225 mg of the expected product in the form of a pale yellow solid (yield=55%).

$^1$H NMR (300 MHz, DMSO) δ: 11.5 (s, 1H); 7.73 (m, 1H); 7.65 (s, 1H); 7.61 (s, 1H); 7.50 (d, J=8.5 Hz, 1H); 7.35 (d, J=8.4 Hz, 1H); 7.12 (d, J=8.4 Hz, 1H); 3.56 (s, 3H); 2.84 (m, 2H); 2.37 (m, 2H); 1.83 (m, 2H).

EXAMPLE 20

5-Chloro-2-(4-chloro-3-fluorophenyl)-1H-indole-3-butanoic Acid

The expected product is obtained in the form of a pale yellow solid (yield=53%) by following a procedure analogous to Example 6 and starting from the ester obtained according to Preparation XXV.

M.p.=182–186° C.

PREPARATION XXVI

Methyl 5-Chloro-2-(3,4-dimethylphenyl)-1H-indole-3-butanoate

The expected product is obtained in the form of a poorly crystalline yellow solid (yield=77%) by following a procedure analogous to Preparation XXV and starting from 3,4-dimethylphenylboronic acid.

$^1$H NMR (300 MHz, CDCl$_3$) δ: 8.02 (s, 1H); 7.57 (d, J=2.0 Hz, 1H); 7.32–7.20 (m, 4H); 7.13 (dd, J=2.0 Hz, J=8.5 Hz, 1H); 3.63 (s, 3H); 2.88 (t, J=7.3 Hz, 2H); 2.34 (m, 8H); 2.01 (quint, J=7.3 Hz, 2H).

EXAMPLE 21

5-Chloro-2-(3,4-dimethylphenyl)-1H-indole-3-butanoic Acid

The expected product is obtained in the form of a yellow solid (yield=90%) by following a procedure analogous to Example 6 and starting from the ester obtained according to Preparation XXVI.

M.p.=130–134° C.

PREPARATION XXVII

Methyl 5-Chloro-2-(3-chloro-4-fluorophenyl)-1H-indole-3-butanoate

The expected product is obtained in the form of an orange solid (yield=31%) by following a procedure analogous to Preparation XXV and starting from 3-chloro-4-fluorophenylboronic acid.

M.p.=90–95° C.

EXAMPLE 22

5-Chloro-2-(3-chloro-4-fluorophenyl)-1H-indole-3-butanoic Acid

The expected product is obtained in the form of an off-white solid (yield=77%) by following a procedure analogous to Example 6 and starting from the ester obtained according to Preparation XXVII.

M.p.=171–175° C.

PREPARATION XXVIII

Ethyl 2-Bromo-5-chloro-1H-indole-3-butanoate

The expected product is obtained in the form of a beige solid (yield=94%) by following a procedure analogous to Preparation XXIV and starting from ethyl 5-chloro-1H-indole-3-butanoate.

M.p.=108–110° C.

PREPARATION XXIX

Ethyl 5-Chloro-2-(3-chlorophenyl)-1H-indole-3-butanoate

The expected product is obtained in the form of a yellow solid (yield=83%) by following a procedure analogous to Preparation XXV and starting from the compound obtained according to Preparation XXVIII and 4-chlorophenylboronic acid.

M.p.=79–81° C.

EXAMPLE 23

5-Chloro-2-(3-chlorophenyl)-1H-indole-3-butanoic Acid

The expected product is obtained in the form of a beige solid (yield=64%) by following a procedure analogous to Example 6 and starting from the ester obtained according to Preparation XXIX.

M.p.=115–116° C.

PREPARATION XXX

Methyl 5-Chloro-2-[4-(trifluoromethyl)phenyl]-1H-indole-3-butanoate

The expected product is obtained in the form of a brown paste (yield=29%) by following a procedure analogous to Preparation XXV and starting from 4-(trifluoromethyl)phenylboronic acid.

$^1$H NMR (300 MHz, DMSO) δ: 11.57 (s, 1H); 7.86 (s, 4H); 7.68 (s, 1H); 7.40 (d, J=8.5 Hz, 1H); 7.14 (d, J=8.5 Hz, 1H); 4.02 (q, J=7.0 Hz, 2H); 2.87 (t, J=6.6 Hz, 2H); 2.35 (t, J=6.6 Hz, 2H); 1.86 (quint, J=6.6 Hz, 2H); 1.15 (t, J=7.0 Hz, 3H).

EXAMPLE 24

5-Chloro-2-[4-(trifluoromethyl)phenyl]-1H-indole-3-butanoic Acid

The expected product is obtained in the form of a white solid (yield=65%) by following a procedure analogous to Example 6 and starting from the ester obtained according to Preparation XXX.

M.p.=132–134° C.

PREPARATION XXXI

Ethyl 5-Chloro-2-(4-fluoro-3-methylphenyl)-1H-indole-3-butanoate

The expected product is obtained in the form of a pale yellow solid (yield=87%) by following a procedure analogous to Preparation XXIX and starting from 4-fluoro-3-methylphenylboronic acid.

M.p.=118–120° C.

EXAMPLE 25

5-Chloro-2-(4-fluoro-3-methylphenyl)-1H-indole-3-butanoic Acid

The expected product is obtained in the form of a pale yellow solid (yield=88%) by following a procedure analogous to Example 6 and starting from the ester obtained according to Preparation XXXI.

M.p.=154–155° C.

PREPARATION XXXII

Methyl 5-Chloro-2-(4-fluoro-3-methylphenyl)-1H-indole-3-butanoate

The expected product is obtained in the form of a yellow paste (yield=88%) by following a procedure analogous to Preparation XXV and starting from 4-chloro-3-methylphenylboronic acid.

$^1$H NMR (300 MHz, CDCl$_3$) δ: 8.01 (s, 1H); 7.57 (d, J=2.2 Hz, 1H); 7.43 (d, J=8.5 Hz, 1H); 7.40 (d, J=1.5 Hz, 1H); 7.30 (dd, J=2.2 Hz, J=8.5 Hz, 1H); 7.23 (d, J=8.5 Hz, 1H); 7.17 (dd, J=1.5 Hz, J=8.5 Hz, 1H); 3.63 (s, 3H); 2.86 (t, J=6.7 Hz, 2H); 2.46 (s, 3H); 2.34 (t, J=6.7 Hz, 2H); 2.00 (quint, J=6.7 Hz, 2H).

EXAMPLE 26

5-Chloro-2-(4-chloro-3-methylphenyl)-1H-indole-3-butanoic Acid

The expected product is obtained in the form of a yellow solid (yield=86%) by following a procedure analogous to Example 6 and starting from the ester obtained according to Preparation XXXII.

M.p.=173–174° C.

PREPARATION XXXIII

Ethyl 5-Chloro-2-(4-nitrophenyl)-1H-indole-3-butanoate

A mixture of 200 mg (0.58.10$^{-3}$ mol) of ethyl 2-bromo-5-chloro-1H-indole-3-butanoate, 498 mg (1.74.10$^{-3}$ mol) of trimethyl(4-nitrophenyl)tin, 140 mg (0.46.10$^{-3}$ mol) of triphenylarsine, 108 mg (0.12.10$^{-3}$ mol) of tris(dibenzylideneacetone)dipalladium and 12 ml of dioxane is prepared and this reaction medium is heated at 50° C. for 6 days, with stirring. After cooling, 12 ml of water are added and the mixture is then extracted with ethyl ether. The organic phase is subsequently washed with water and then dried and concentrated under reduced pressure. The residue is purified by chromatography on silica gel using a petroleum ether/ethyl acetate mixture (85/15; v/v) as the eluent. The fractions containing the expected compound are purified again by reversed phase chromatography on C$_{18}$-grafted silica using an acetonitrile/water mixture (7/3; v/v) as the eluent to give 70 mg of the expected compound in the form of a yellow paste (yield=31%).

$^1$H NMR (300 MHz, DMSO) δ: 11.70 (s, 1H); 8.38 (d, J=8.8 Hz, 2H); 7.93 (d, J=8.8 Hz, 2H); 7.72 (d, J=1.8 Hz, 1H); 7.42 (d, J=8.8 Hz, 1H); 7.18 (dd, J=1.8 Hz, J=8.8 Hz, 1H); 4.05 (q, J=7.0 Hz, 2H); 2.95 (m, 2H); 2.40 (m, 2H); 1.85 (m, 2H); 1.16 (t, J=7.0 Hz, 3H).

EXAMPLE 27

5-Chloro-2-(4-nitrophenyl)-1H-indole-3-butanoic Acid

The expected product is obtained in the form of a yellow solid (yield=99%) by following a procedure analogous to Example 6 and starting from the ester obtained according to Preparation XXXIII.

M.p.=234–235° C.

PREPARATION XXXIV

Methyl 5-Chloro-2-(3-thienyl)-1H-indole-3-butanoate

The expected product is obtained in the form of a yellow solid (yield=28%) by following a procedure analogous to Preparation XXV and starting from 3-thienylboronic acid.

M.p.=65–68° C.

EXAMPLE 28

5-Chloro-2-(3-thienyl)-1H-indole-3-butanoic Acid

The expected product is obtained in the form of a yellow solid (yield=67%) by following a procedure analogous to Example 6 and starting from the ester obtained according to Preparation XXXIV.

M.p.=145–150° C.

PREPARATION XXXV

Methyl 5-Chloro-1H-indole-3-propionate

A solution of 232 mg ($1.04.10^{-3}$ mol) of 5-chloro-1H-indole-3-propionic acid in 14 ml of ethanol is prepared and 4.4 ml ($8.8.10^{-3}$ mol) of a 2 M solution of (trimethylsilyl) diazomethane in hexane are added at room temperature. The reaction medium is stirred for 15 min, 1 g of silica is then added and the mixture is then filtered. The filtrate is concentrated under reduced pressure and the residue is purified by chromatography on silica gel using a methylcyclohexane/ethyl acetate mixture (2/1; v/v) as the eluent to give 225 mg of the expected product in the form of a yellow solid (yield=91%).

M.p.=86° C.

PREPARATION XXXVI

Methyl 2-Bromo-5-chloro-1H-indole-3-propionate

The expected product is obtained in the form of a brown oil (yield=77%) by following a procedure analogous to Preparation XXIV and starting from the ester obtained according to Preparation XXXV.

$^1$H NMR (300 MHz, DMSO) δ: 11.90 (s, 1H); 7.58 (d, J=1.9 Hz, 1H); 7.28 (d, J=8.5 Hz); 7.08 (dd, J=1.9 Hz, J=8.5 Hz, 1H); 3.56 (s, 3H); 2.91 (t, J=7.5 Hz, 2H); 2.57 (t, J=7.5 Hz, 2H).

PREPARATION XXXVII

Methyl 5-Chloro-2-[4-(trifluoromethyl)phenyl]-1H-indole-3-propionate

The expected product is obtained in the form of a colorless oil (yield=35%) by following a procedure analogous to Preparation XXX and starting from the brominated derivative obtained according to Preparation XXXVI.

$^1$H NMR (300 MHz, CDCl$_3$) δ: 8.11 (s, 1H); 7.76 (d, J=8.2 Hz, 2H); 7.68 (d, J=8.2 Hz, 2H); 7.62 (s, 1H); 7.32 (d, J=8.6 Hz, 1H); 7.21 (d, J=8.6 Hz, 1H); 3.65 (s, 3H); 3.22 (t, J=8 Hz, 2H); 2.68 (t, J=8 Hz, 2H).

EXAMPLE 29

5-Chloro-2-[4-(trifluoromethyl)phenyl]-1H-indole-3-propionic Acid

The expected product is obtained in the form of a beige solid (yield=76%) by following a procedure analogous to Example 6 and starting from the ester obtained according to Preparation XXXVII.

M.p.=218° C.

PREPARATION XXXVIII

Methyl 5-Chloro-2-(3,5-dimethyl4-fluorophenyl)-1H-indolebutanoate

The expected product is obtained in the form of a thick yellow oil (yield=45%) by following a procedure analogous to Preparation XXV and starting from 3,5-dimethyl-4-fluorophenylboronic acid.

NMR (300 MHz, DMSO) δ: 11.35 (s, 1H); 7.60 (s, 1H); 7.35 (m, 3H); 7.10 (d, 1H); 3.60 (s, 3H); 2.82 (t, 2H); 2.40 (t, 2H); 2.35 (s, 6H); 1.85 (m, 2H).

The 3,5-dimethyl-4-fluorophenylboronic acid is obtained with a yield of 22% by a process analogous to the preparation of the phenylboronic derivatives, namely by successively reacting n-BuLi and then isopropyl borate with 5-bromo-2-fluoro-1,3-dimethylbenzene.

NMR (300 MHz, DMSO) δ: 7.95 (s, 1H); 7.50 (d, 2H); 6.50 (s, 1H); 2.20 (s, 3H).

EXAMPLE 30

5-Chloro-2-(3,5-dimethyl-4-fluorophenyl)-1H-indolebutanoic Acid

The expected product is obtained in the form of a pale yellow solid (yield=71%) by following a procedure analogous to Example 6 and starting from the ester obtained according to Preparation XXXVIII.

M.p.=58° C.

PREPARATION XXXIX

Methyl 5-Chloro-2-[4-chloro-3-(trifluoromethyl)phenyl]-1H-indolebutanoate

The expected product is obtained in the form of a beige oil (yield=41%) by following a procedure analogous to Preparation XXV and starting from 4-chloro-3-(trifluoromethyl) phenylboronic acid.

NMR (300 MHz, DMSO) δ: 11.62 (s, 1H); 8.05 (s, 1H); 7.95 (d, 1H); 7.85 (d, 1H); 7.70 (s, 1H); 7.40 (d, 1H); 7.15 (d, 1H); 3.60 (s, 3H); 2.85 (t, 2H); 2.35 (t, 2H); 1.85 (m, 2H).

EXAMPLE 31

5-Chloro-2-[4-chloro-3-(trifluoromethyl)phenyl]-1H-indolebutanoic Acid

The expected product is obtained in the form of a white solid (yield=88%) by following a procedure analogous to Example 6 and starting from the ester obtained according to Preparation XXXIX.

M.p.=158–160° C.

Table I summarizes the formulae of the compounds described above.

TABLE I

R1—[indole with (CH2)n—CO2H at 3-position, N-H, 2-substituted with phenyl ring bearing R2, R3, X, R4]

| Example | X | R1 | n | R2 | R3 | R4 |
|---|---|---|---|---|---|---|
| 1 | —C=C— | Br | 3 | H | H | H |
| 2 | —C=C— | Cl | 2 | H | H | H |
| 3 | —C=C— | Cl | 3 | H | H | H |
| 4 | —C=C— | F | 3 | H | H | H |
| 5 | —C=C— | CF3 | 3 | H | H | H |
| 6 | —C=C— | Cl | 2 | 4-F | H | H |
| 7 | —C=C— | Cl | 2 | 4-Cl | H | H |
| 8 | —C=C— | Cl | 2 | 4-CH3 | H | H |
| 9 | —C=C— | Cl | 3 | 4-Cl | H | H |
| 10 | —C=C— | Cl | 3 | 3-Cl | 4-Cl | H |
| 11 | —C=C— | CH3 | 3 | H | H | H |
| 12 | —C=C— | Cl | 3 | 4-F | H | H |
| 13 | —C=C— | Cl | 3 | * | * | H |
| 14 | —C=C— | NO2 | 3 | H | H | H |
| 15** | —C=C— | Cl | 3 | 4-F | H | H |
| 16 | —C=C— | Cl | 2 | 3-Cl | 4-Cl | H |
| 17 | —C=C— | Cl | 3 | 4-Br | H | H |
| 18 | —C=C— | Cl | 3 | 4-CN | H | H |
| 19 | —C=C— | Cl | 3 | 3-F | 4-F | H |
| 20 | —C=C— | Cl | 3 | 3-F | 4-Cl | H |
| 21 | —C=C— | Cl | 3 | 3-CH3 | 4-CH3 | H |
| 22 | —C=C— | Cl | 3 | 3-Cl | 4-F | H |
| 23 | —C=C— | Cl | 3 | 3-Cl | H | H |
| 24 | —C=C— | Cl | 3 | 4-CF3 | H | H |
| 25 | —C=C— | Cl | 3 | 3-CH3 | 4-F | H |
| 26 | —C=C— | Cl | 3 | 3-CH3 | 4-Cl | H |
| 27 | —C=C— | Cl | 3 | 4-NO2 | H | H |
| 28 | S | Cl | 3 | H | H | H |
| 29 | —C=C— | Cl | 2 | 4-CF3 | H | H |
| 30 | —C=C— | Cl | 3 | 3-CH3 | 4-F | 5-CH3 |
| 31 | —C=C— | Cl | 3 | 3-CF3 | 4-Cl | H |

*R2 and R3 form a 2-naphthyl group with the phenyl
**sodium salt of Example 12

Biological Activity

The inhibitory effects of the compounds described in the present invention on the chemokines IL-8 and Gro-alpha were determined by the following in vitro tests:

A) IL-8 Receptor Binding Test

Human IL-8 labeled with iodine 125 ($[^{125}I]$-IL-8) was obtained from NEN (Les Ulis) and has a specific activity of 2.200 Ci/mmol. The recombinant human CXCR2 receptor was expressed in HEK 293 cells (ATCC, CRL-1573), K-562 cells (ATCC, CCL-243) or THP-1 cells (ATCC, TIB-202). The HEK 293 cells are maintained in culture in DMEM (GIBCO) containing 4.5 g/l of glucose, 10% of fetal calf serum, 1% of Glutamax, 1% of non-essential amino acids, 1 mM sodium pyruvate, 100 IU/ml of penicillin and 100 μg/ml of streptomycin. The K-562 and THP-1 cells are maintained in culture in RPMI1640 medium (GIBCO) containing 10% of fetal calf serum, 1% of non-essential amino acids, 1 mM sodium pyruvate, 100 IU/ml of penicillin and 100 μg/ml of streptomycin. The cells are used when the cultures have reached 80% confluence.

The membranes are prepared according to the previously described protocol (Bastian et al., *Br. J. Pharmacol.*, 1997, 122, 393–399), except that the homogenization buffer has been replaced with a saline solution, buffered to pH 8.0, containing 20 mM Tris, 1.2 mM $MgSO_4$, 0.1 mM EDTA and 25 mM NaCl. The competition experiments are performed in plates comprising 96 wells of 1 ml, at room temperature, the final volume being 0.25 ml. The membranes, diluted in a solution of 20 mM bis-trispropane and 0.4 mM Tris-HCl, buffered to pH 8.0, containing 1.2 mM $MgSO_4$, 0.1 mM EDTA, 25 mM NaCl and 0.03% of CHAPS, are incubated with decreasing concentrations of the test compound (from 100 μM to 0.01 nM) and 150 pM $[^{125}I]$-IL-8. The non-specific binding is determined in the presence of 300 nM unlabeled IL-8. After 60 min of incubation at room temperature, the reaction is stopped by rapid filtration under vacuum on a GF/C Whatman filter incubated beforehand for 1 hour at +4° C. in a solution of 1% (weight/volume) of polyethyleneimine and 0.5% (weight/volume) of BSA. The filters are washed with a solution containing 25 mM NaCl, 1 mM $MgSO_4$, 0.5 mM EDTA and 10 mM Tris-HCl, buffered to pH 7.4. The radioactivity retained on the filters is measured in a gamma counter.

The affinities of the compounds described in the present invention were also determined by a whole cell binding test. The transfected THP-1 or K-562 cells are suspended in the binding test buffer (calcium-free and magnesium-free PBS containing 0.5% (weight/volume) of BSA, pH 7.4) at a rate of $2.5 \times 10^6$ cells/ml. The competition experiments are performed in plates comprising 96 wells of 1 ml, the final volume being 0.25 ml. $0.5 \times 10^6$ cells are incubated with decreasing concentrations of the test compound (100 μM to 0.01 nM) and 150 pM $[^{125}I]$-IL-8. The non-specific binding is determined in the presence of 300 nM non-radiolabeled chemokine. After 90 min of incubation at +4° C., the reaction is stopped by rapid filtration under vacuum on a GF/C Whatman filter incubated beforehand for 1 h in a solution of 3% (weight/volume) of polyethyleneimine. The filters are washed with a solution of PBS containing 0.5 M NaCl, at pH 7.4. The radioactivity contained in the filters is measured in a gamma counter.

The compounds of formula I described in the present invention, tested at a concentration of 10 μM, inhibit the binding of the $[^{125}I]$-IL-8 to the CXCR2 receptor by at least 95%.

B) Measurement of the Calcium Flux

The effects of the compounds of the present invention were evaluated on the calcium flux induced by IL-8 or Gro-alpha.

THP-1 cells expressing the recombinant CXCR2 receptors, U937 cells differentiated with 1% (volume/volume) of DMSO (dimethyl sulfoxide) or Eol3 cells are incubated in the presence of the fluorescent indicator Fura-2 AM at a concentration of 5 μM for 1 h at 37° C. After this loading period, the cells are washed and suspended at a concentration of $1 \times 10^6$ cells/ml in a saline solution containing 136 mM NaCl, 4.7 nM KCl, 1.2 mM $MgSO_4$, 1.6 mM $CaCl_2$, 1.2 mM $KH_2PO_4$, 11 mM glucose and 5 mM HEPES, at pH 7.4. The cellular suspension (2 ml) is placed in a quartz cuvette and the intensity of fluorescence at 510 nm is measured on an LS50B spectrofluorimeter (Perkin-Elmer) after alternate excitations at 340 nm and 380 nm. The ratio of the intensities of fluorescence after excitation at 340 nm and 380 nm is determined and the intracellular calcium concentration is calculated according to the following formula:

$$[Ca^{2+}]i = K_d \frac{(R - R\min)}{(R\max - R)}(Sf2/Sb2)$$

in which:

$K_d$ is the affinity constant of the Fura-2/calcium complex,
Rmax is the maximum intensity of fluorescence determined after the addition of the ionophore Bromo-A23187 at 1 μM, Rmin is the minimum ratio determined after the addition of 10 mM EGTA following the addition of the ionophore, and Sf2/Sb2 is the ratio of the fluorescence values under excitation at 380 nm, determined at Rmin and Rmax respectively.

After a stabilization period of 1 min, during which the basal intracellular calcium concentration is determined, the test compound or the control vehicle is added to the cells. After an incubation period of 2 min, during which the calcium concentration is measured, the cells are stimulated with the different agonists (IL-8 or Gro-alpha). The calcium concentration is measured for 2 min.

The compounds of formula I described in the present invention inhibit the calcium release induced by IL-8 or Gro-alpha.

The activity of the compounds according to the invention, revealed in the biological tests, signifies an antagonistic action towards IL-8 and makes it possible to envisage their use in therapeutics.

According to the invention, it is recommended to use the compounds of formula I as active principles of drugs for a preventive or curative treatment in mammals, especially man, for diseases which involve IL-8 and/or chemokines of the same family and are generally characterized by a massive invasion of neutrophils.

Among the diseases which can be treated by administering a therapeutically sufficient amount of at least one compound of formula I, there may be mentioned rheumatoid polyarthritis, psoriasis or atypical dermatitis, diseases associated with pathological angiogenesis (such as cancer), tumoral cell proliferation and metastasis formation (for example in the case of melanoma), asthma, chronic obstruction of the lungs, acute respiratory distress syndrome, inflammation of the colon, Crohn's disease, ulcerative colitis, gastric ulcer, septic shock, endotoxin shock, septicemia caused by Gram(-) bacteria, toxic shock syndrome, cerebral ischemia, cardiac or renal ischemia/reperftision phenomena, glomerulonephritis, thrombosis, atheroma, Alzheimer's disease, graft versus host reactions or allograft rejections.

The compounds of formula I have to be administered in a sufficient amount to antagonize IL-8 by binding competitively to the receptors. The dose of active principle depends on the mode of administration and the type of pathological condition and is generally between 0.01 and 10 mg/kg. The compounds of formula I can also be associated with another active principle.

Within the framework of their therapeutic use, the compounds of formula I will generally be administered in a variety of forms in association with the commonly used excipients.

The formulation used may be an oral form, for example gelatin capsules, tablets containing the solid active principle in powdered or micronized form, a syrup or a solution in which the active principle is present in solution, suspension, emulsion or microemulsion.

The formulation can also be presented in a form which can be administered for topical use, for example a cream, a lotion or a transdermal device such as an adhesive patch. The active principle can also be formulated for a mode of administration by subcutaneous, intramuscular or intravenous injection.

What is claimed is:

1. A compound which is selected from the group consisting of:

i) a compound of the formula

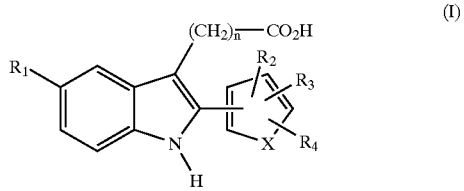

in which:
X is a double bond —C═C— or a sulfur atom;
$R_1$ is a halogen, a nitro group, a trifluoromethyl group or a $C_1$–$C_3$ alkyl group;
$R_2$, $R_3$ and $R_4$ are each independently a hydrogen atom, a halogen, a $C_1$–$C_3$ alkyl group, a nitro group, a trifluoromethyl group or a cyano group, or $R_2$ and $R_3$ form a fused aromatic ring together with the aromatic ring to which they are attached; and
n is equal to 2 or 3; and ii) esters of the compounds of formula I and addition salts of said compounds with a mineral or organic base.

2. A compound of formula (I) according to claim 1 in which X is a double bond —C═C—, which is selected from the group consisting of:

i) a compound of the formula

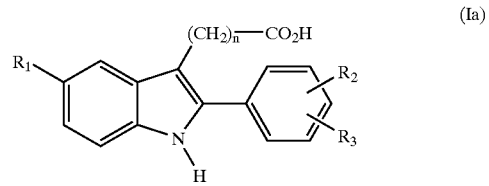

in which:
$R_1$ is a halogen, a nitro group, a trifluoromethyl group or a $C_1$–$C_3$ alkyl group;
$R_2$ and $R_3$ are each independently a hydrogen atom, a halogen or a $C_1$–$C_3$ alkyl group, or they form a fused aromatic ring together with the phenyl ring to which they are attached; and
n is equal to 2 or 3; and ii) esters of the compounds of formula I and addition salts of said compounds with a mineral or organic base.

3. A compound according to claim 1 wherein $R_2$ is selected from the group consisting of a hydrogen atom, a chlorine atom, a fluorine atom and a methyl group; $R_3$ is a chlorine atom or a fluorine atom and $R_4$ is a hydrogen atom.

4. A compound according to claim 1, wherein X is a double bond —C═C— and $R_2$ and $R_3$ form a naphthyl group together with the phenyl ring to which they are attached.

5. A compound according to claim 2, wherein $R_2$ and $R_3$ form a naphthyl group together with the phenyl ring to which they are attached.

6. A compound according to claim 1 wherein $R_1$ is a chlorine atom.

7. A therapeutic composition which contains, in association with a physiologically acceptable excipient, a compound of formula (I) according to claim 1, or one of its pharmaceutically acceptable salts.

8. A method for the treatment of diseases involving an overexpression of IL-8 and/or chemokines of the same family, which comprises administering to a mammal in need thereof an effective amount of a compound of formula (I) according to claim 1, or one of its pharmaceutically acceptable salts.

* * * * *